United States Patent

Gialdi et al.

[11] 4,036,963
[45] July 19, 1977

[54] DERIVATIVES OF QUINOLINE-8-CARBOXYLIC ACID HAVING PESTICIDAL ACTION

[75] Inventors: Franco Gialdi, Pavia; Angelo Longoni; Giannantonio Michieli, both of Milan; Riccardo Ponci, Pavia, all of Italy

[73] Assignee: Montedison Fibre S.p.A., Milan, Italy

[21] Appl. No.: 494,976

[22] Filed: Aug. 5, 1974

[30] Foreign Application Priority Data

Aug. 6, 1973  Italy .................................. 27580/73

[51] Int. Cl.² .......................... C07D 215; A61K 31/47
[52] U.S. Cl. ............................. 424/258; 260/268 BQ; 260/270 C; 260/287 G
[58] Field of Search .......... 260/287 G, 287 L, 287 F; 424/258

[56] References Cited

U.S. PATENT DOCUMENTS

| | | | |
|---|---|---|---|
| 2,864,823 | 12/1958 | Schwechten et al. | 260/287 G |
| 3,632,590 | 1/1972 | Leroi | 260/287 R |
| 3,853,955 | 12/1974 | Dijk et al. | 260/287 L |

OTHER PUBLICATIONS

Lachowicz et al., "Chemical Abstracts," vol. 69, 1968, 2844b.

Primary Examiner—Donald G. Daus
Assistant Examiner—David E. Wheeler

[57] ABSTRACT

Derivatives of quinoline-8-carboxylic acid having pesticidal action are disclosed, as are compositions comprising such derivatives.

The quinoline-8-carboxylic acid derivatives which we have found to be effective pesticides include such derivatives having the general formula:

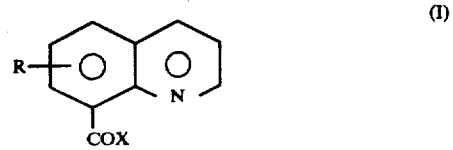

in which
R represents H, halogen, $C_1$–$C_3$ alkyl, $C_2$–$C_6$ alkenyl, $CF_3$, $C_1$–$C_3$- alkoxyl or $C_1$–$C_3$- alkythio;
X represents the group OY, in which Y is H, $C_1$–$C_6$ alkyl, $C_2$–$C_6$ alkenyl, $C_2$–$C_6$ alkinyl optionally substituted, an alkali metal, an alkaline earth metal, a transition metal, Mn, $NR_2$ in which both R equal or different have the same significance as above or are pyridines, aryl or alkyl or aralkylamines; and the quaternarized nitrogen salts of said compounds.

The compounds having formula: I. are distinguished by having good activity as pesticides and, in particular, as insecticides.

2 Claims, No Drawings

DERIVATIVES OF QUINOLINE-8-CARBOXYLIC ACID HAVING PESTICIDAL ACTION

THE PRESENT INVENTION

The present invention concerns the use as pesticide agents of a class of compounds derived from quinoline-8-carboxylic acids, the compositions containing said compounds and the use of said compositions for the same purposes.

The compounds according to the invention belong to the class of the formula:

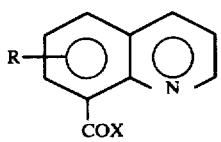

in which
R represents H, halogen, $C_1$–$C_3$ alkyl, $C_2$–$C_6$ alkenyl, $CF_3$, $C_1$–$C_3$ - alkoxyl or $C_1$–$C_3$ - alkythio;
X represents the group OY, in which Y is H, $C_1$–$C_6$ alkyl, $C_2$–$C_6$ alkenyl, $C_2$–$C_6$ alkinyl optionally substituted, an alkali metal, an alkaline earth metal, a transition metal, Mn, $NR_2$ in which both R equal or different have the same significance as above or are pyridines, aryl or alkyl or aralkylamines; and the quarternarized nitrogen salts of said compounds.

Under the scope of this invention fall also the compositions containing as an active principle compounds according to this invention, such as wettable powders, emulsifiable oil, the granular and powdery formulates. The preparation of these compositions may be realized by operating according to the procedures known to the Prior Art.

The following examples are given to evidence the essential aspects of the invention, useful for an easy and precise understanding of the subject. However it must be understood that there may be introduced obvious variants to the technique of preparation of the compounds of the invention, variants, that is, in the use and in the method of application, without thereby deviating from the principle and protective scope of the invention.

EXAMPLE 1

Into a reactor fitted with a stirrer, a thermometer, a refluxer, a separating funnel and a heating bath, the following substances were introduced:
  0.1 mole of anthranilic acid;
  0.15 mole of glycerine; and
  a quantity of 85% sulphuric acid equal to the weight of the anthranilic acid.

This mass was stirred and slowly heated up to a temperature of 100° C, after which the heating was continued up to a temperature comprised between 140° and 150 ° C at which the reaction started.

The reaction was lively and developed considerable heat. The mass was stirred for about 1 hour. Once the reaction was complete, 0.12 mole of metha-nitro-phenyl-sulphonic acid was added and the mass was refluxed for 4.5 hours. It was allowed to cool down and then poured into $H_2O$, from which the reaction product was extracted with methylene chloride. The extract was repeatedly washed with $H_2O$; the solvent was then evaporated at reduced pressure and the extract was left to crystallize at room temperature.

The residue obtained, when re-crystallized, had a melting point of 189° C and consisted of quinoline-8-carboxylic acid.

EXAMPLES 2 – 19

By operating as described in Example 1, but suitably varying the reactants, and/or carrying out successive reactions known in the art, the products reported in the following table were obtained.

TABLE

| Ex. | Compound | Physical-chemical Characteristics and Bibliography |
|---|---|---|
| 2 | (structure: quinoline with $CH_3$ and COOH substituents) | melt. point 169° C (Chem. Zentralblatt 1934 I 1328–29) |
| 3 | (structure: quinoline with $OCH_3$, HO–C(=O)–, and N$^+$–$CH_3$ substituents) $I^-$ | decomposition at 220° C |
| 4 | (structure: quinoline with $COO/_2Zn$ substituent) | — |

TABLE-continued

| Ex. | Compound | Physical-chemical Characteristics and Bibliography |
|---|---|---|
| 5 | quinoline-8-COO⁻ · H₂⁺N—(1,4-diazepane)—NCH₃ | melt. point 185° C |
| 6 | quinoline-8-COONa | melt. point >250° C |
| 7 | quinoline-8-CONH₂ | melt. point 171°–173° C |
| 8 | (quinoline-8-COO)₂Cu | — |
| 9 | quinoline-8-COOC₂H₅ | melting point 44° C |
| 10 | quinoline-8-COO⁻, NH(C₄H₉ sec.)₂⁺ (on ring N) | melting point 190° C |
| 11 | quinoline-8-COO⁻, N⁺H·CH₂—pyridine | melting point 192° C |
| 12 | quinoline-8-COO⁻, N⁺H·CH₂—C₆H₃(O—CH₂—O)(CH₃) (piperonyl/methylenedioxyphenyl) | melting point 155° C |
| 13 | (quinoline-8-COO)₂Mn | — |
| 14 | (quinoline-8-COO)₂Co | — |

TABLE-continued

| Ex. | Compound | Physical-chemical Characteristics and Bibliography |
|---|---|---|
| 15 | quinoline-8-carboxylate with dicyclohexylammonium | melting point 170–175° C |
| 16 | quinoline-8-carboxylate with 2,4,5-trichloroanilinium | melting point 120–130° C |
| 17 | [8-(methoxycarbonyl)quinolinium] iodide | melting point 210° C dec. |
| 18 | 5-chloroquinoline-8-carboxylic acid | melting point 228–229°C (cfr. Lachowicz A. et al; Rocz. Chem. 1967 41(9) pp. 1543–59) |
| 19 | quinoline-8-carboxylate with bis(2-hydroxyethyl)ammonium | — |

EXAMPLE 20

*Macrosiphum solani*

Small potato plants, grown in pots, were contaminated with adult aphis females of the indicated species and, after a few hours, were sprayed with an aqueous dispersion of pecticides according to the invention. The percentages of mortality 24 hours after the teatment are shown in the following table.

| Compound No. | Percentual mortality at a concentration of: | |
|---|---|---|
| | 0.1% of active subst. | 0.01% of active sub. |
| 2 | 100 | 84 |
| 5 | 100 | 95 |
| 9 | 100 | 88 |
| 10 | 100 | 84 |
| 11 | 100 | 85 |
| 13 | 100 | 68 |

EXAMPLE 21

*Aphis fabae*

Small broad bean plants grown in pots were contaminated with young stage and adult aphides of the species indicated and, after a few hours, were sprayed with an aqueous dispersion of pecticides according to the invention. The mortality percentages 24 hours after the treatment are shown in the following Table.

| Compound No. | Percentual mortality at a concentration of: | |
|---|---|---|
| | 0.1% of active subst. | 0.01% of active sub. |
| 1 | 100 | 89 |
| 2 | 100 | 84 |
| 6 | 100 | 80 |
| 8 | 100 | 88 |
| 19 | 100 | 82 |

EXAMPLE 22

*Leptinotarsa decemlineata*

Small potato plants grown in pots and contaminated with 4-day old larvae of the indicated species were sprayed with an aqueous dispersion of a pesticide according to the invention. The following Table reports the mortality in percent of the larvae 48 hours after the treatment.

| Compound No. | Percentual mortality at a concentration of: | | |
|---|---|---|---|
| | 0.1% active sub | 0.05% active sub. | 0.01% active sub. |
| 1 | 100 | 88 | 30 |
| 2 | 100 | 100 | 87 |
| 5 | 100 | 100 | 0 |
| 11 | 100 | 97 | 0 |

EXAMPLE 23

*Pieris brassicae*

Cut cauliflower leaves were sprayed with an aqueous dispersion of pesticides according to the invention and, after drying, were contaminated with 5-day old larvae of the species indicated. The following Table reports the mortality in percent of the larvae 48 hours after the treatment.

| Compound No. | Percentual mortality at a concentration of: | | |
|---|---|---|---|
| | 0.1% active sub. | 0.05% active sub. | 0.01% active sub |
| 1 | 85 | 23 | 0 |
| 2 | 100 | 100 | 83 |
| 3 | 100 | 100 | 55 |

EXAMPLE 24

*Spodoptera littoralis*

Cut tobacco leaves were sprinkled with an aqueous dispersion of the compounds listed in the following Table, and after being dried were infected with 5-days old larvae of *Spodotera littoralis*.

| Compound No. | Percentual mortality at a concentration of: | | |
|---|---|---|---|
| | 0.1% active sub. | 0.05% active sub. | 0.01% active sub. |
| 2 | 100 | 100 | 75 |
| 9 | 100 | 90 | 25 |
| 3 | 100 | — | — |

We claim:

1. A composition for combatting infestations due to Macrosiphum solani, Aphis fabae, Leptinotarsa decemlineata, Pieris brassicae, and Spodoptera littoralis, said composition consisting essentially of an aqueous dispersion of at least 0.05% by weight of an insecticide having the formula

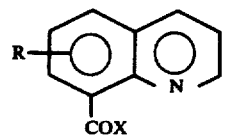

in which
R is selected from the group consisting of H, halogen, and alkyl groups having from 1 to 3 carbon atoms; and
X represents $NH_2$ or OY in which Y is selected from the group consisting of H, alkaline metals, alkaline earth metals; amines, and their quinoline salts with inorganic acids; and n-alkyl quinolinium salts.

2. The method of combatting infestations due to Macrosiphum solani, Aphis Labae, Leptinotarsa decemlineate, Pieris brassicae, and Spodoptera littoralis, which consists in applying to the habitat of said insects an aqueous dispersion of at least 0.5% of an insecticide having the formula

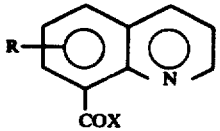

in which
R is selected from the group consisting of H, halogen, and alkyl groups having from 1 to 3 carbon atoms; and
X represents $NH_2$ or OY in which Y is selected from the group consisting of H, alkaline metals, alkaline earth metals, amines, and their quinoline salts with inorganic acids and n-alkyl quinolinium salts.

* * * * *